(12) United States Patent
Vartiainen et al.

(10) Patent No.: US 10,835,441 B2
(45) Date of Patent: Nov. 17, 2020

(54) PATIENT POSITIONING APPARATUS WITH ADJUSTABLE AND LOCKABLE BACK REST

(71) Applicant: PaloDEx Group OY, Tuusula (FI)

(72) Inventors: Sami Vartiainen, Vantaa (FI); Jorma Savolainen, Helsinki (FI); Markku Huovinen, Riihimäki (FI); Wycliffe Raduma, Espoo (FI); Antti Korpela, Kerava (FI); Antti Karhunen, Helsinki (FI); Markus Rintamäki, Tuusula (FI); Juho Malin, Lahela (FI); Saku Leponokka, Riihimäki (FI)

(73) Assignee: PALODEX GROUP OY, Tuusula (FI)

( * ) Notice: Subject to any disclaimer, the term of this patent is extended or adjusted under 35 U.S.C. 154(b) by 159 days.

(21) Appl. No.: 15/964,616

(22) Filed: Apr. 27, 2018

(65) Prior Publication Data

US 2019/0328600 A1    Oct. 31, 2019

(51) Int. Cl.
| | | |
|---|---|---|
| *A61B 6/04* | (2006.01) | |
| *A61G 15/02* | (2006.01) | |
| *A47C 1/027* | (2006.01) | |
| *A47C 3/18* | (2006.01) | |
| *A47C 3/20* | (2006.01) | |
| *A61B 6/14* | (2006.01) | |

(52) U.S. Cl.
CPC ............. *A61G 15/02* (2013.01); *A47C 1/027* (2013.01); *A47C 3/18* (2013.01); *A47C 3/20* (2013.01); *A61B 6/0478* (2013.01); *A61B 6/14* (2013.01)

(58) Field of Classification Search
CPC ...... A61G 15/00; A61G 15/002; A61G 15/02; A61G 15/12; A61G 15/125; A47C 1/027; A47C 3/18; A47C 3/20; A61B 6/04; A61B 6/0478; A61B 6/14
USPC .................................. 378/38, 39, 40, 68, 208
See application file for complete search history.

(56) References Cited

U.S. PATENT DOCUMENTS 3,578,379 A * 5/1971 Taylor ..................... A47C 1/03
297/71
4,229,656 A   10/1980 Iversen et al.

FOREIGN PATENT DOCUMENTS

| JP | S55-151311 U | 10/1980 |
| JP | S61-205509 U | 12/1986 |
| JP | 2009-072508 A | 4/2009 |
| JP | 2014-064781 A | 4/2014 |
| WO | 2004/082481 A1 | 9/2004 |

OTHER PUBLICATIONS

International Search Report and Written Opinion for Application No. PCT/EP2019/056957 dated May 16, 2019 (12 pages).

* cited by examiner

*Primary Examiner* — Jurie Yun
(74) *Attorney, Agent, or Firm* — Michael Best & Friedrich LLP

(57) ABSTRACT

A patient positioning apparatus for an X-ray dental imaging system includes a head rest and a chair separate from and spaced from the head rest. The chair has a seat portion and a back rest coupled to the seat portion. The chair further includes a locking system that locks a position of the back rest relative to the seat portion.

16 Claims, 8 Drawing Sheets

PATIENT POSITIONING APPARATUS WITH ADJUSTABLE AND LOCKABLE BACK REST

FIELD OF THE INVENTION

Embodiments relate to patient positioning apparatuses, and more particularly to patient positioning apparatuses for X-ray dental imaging systems.

SUMMARY OF THE INVENTION

X-ray imaging in medical (for example, dental) fields requires that a patient be positioned with respect to an X-ray imaging device so that an image of an anatomical feature or anatomy of interest may be obtained. Improper positioning of a patient may result in an image that fails to include the anatomy of interest. Patient movement may also cause this problem, and may also cause artifacts. In some instances, it is preferred that a patient sit during an imaging procedure. For example, the longer an imaging takes, the easier it is to keep a patient still when he or she is sitting. In other instances, patients may be incapable of standing, for example, patients who have neurological disorders or injuries, or are older or weaker, or patients such as children that may benefit from sitting rather than being asked to stand for long periods of time. Thus, operators may prefer that patients be seated during certain imaging procedures, for example computed tomography ("CT") scans.

However, because human bodies are different in size and shape, it is challenging to position a patient's head to a desired position for each patient. Thus, embodiments and examples described herein provide, among other things, patient positioning apparatuses for sitting patients.

In one aspect, embodiments provide a patient positioning apparatus for an X-ray dental imaging system. The patient positioning apparatus includes a head rest and a chair separate from and spaced from the head rest. The chair has a seat portion and a back rest coupled to the seat portion. The chair further includes a locking system configured to lock a position of the back rest relative to the seat portion. The adjustments modifying the relative positions of the seat portion, back rest, and head rest accommodate large anatomical variations in the bodies and backs of patients. The head rest may be tied to or otherwise correspond to an imaging area and it may be adjustable to a limited degree, to account for head size variations which may be relatively close from patient to patient as compared to larger anatomical variations in the bodies and backs of patients.

Other features and aspects of will become apparent by consideration of the following detailed description and accompanying drawings.

Figure 1:
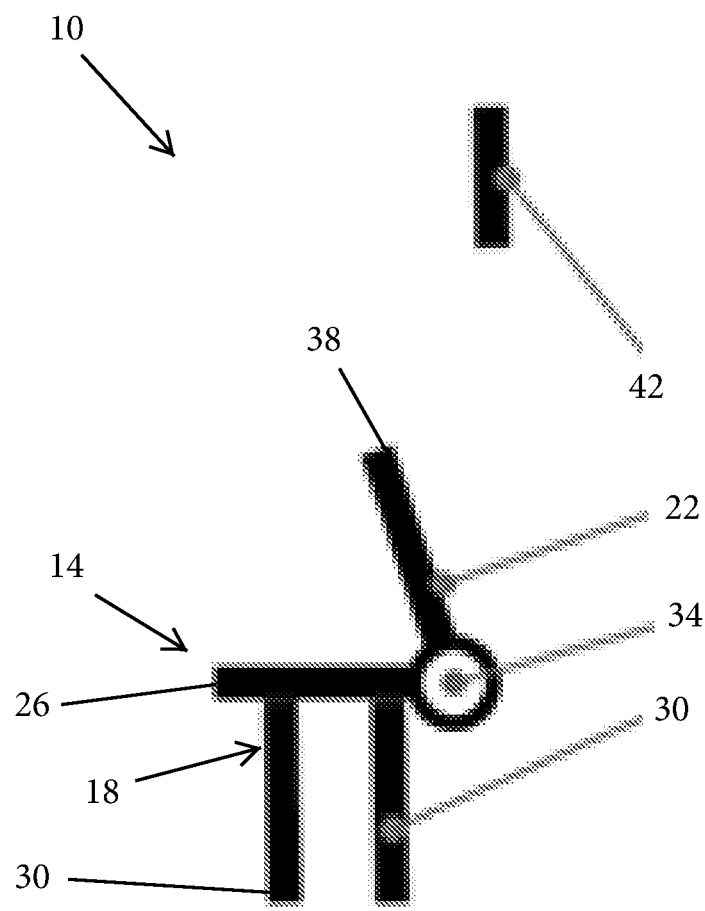
FIG. 1 is a schematic view of a patient positioning apparatus according to one embodiment, shown without a patient.

Before any embodiments are explained in detail, it is to be understood that they are not limited in their application to the details of construction and the arrangement of components set forth in the following description or illustrated in the following drawings. Other embodiments are possible and embodiments are capable of being practiced or of being carried out in various ways. Also, it is to be understood that the phraseology and terminology used herein is for the purpose of description and should not be regarded as limiting.

DETAILED DESCRIPTION

A patient positioning apparatus 10 is shown in FIGS. 1-6. The apparatus 10 includes a chair 14 having a seat portion 18 and a back rest 22 pivotally coupled to the seat portion 18.

The seat portion 18 includes a support member 26 (for example, a generally horizontal member) that is sized and shaped for a patient to sit on, as well as seat legs 30 extending below the support member 26 that support the support member 26. The seat portion 18 may include less than two seat legs 30, more than two seat legs 30, or no seat legs 30. For example, the seat portion 18 may be a structure (for example, a solid structure) that extends entirely to a floor surface or base surface without legs, or may be a structure that extends (for example, horizontally or cantilevered) above the floor surface or base surface from a component (for example, a column, frame, or base) of an X-ray dental imaging system.

The chair 14, or portions thereof, may be adjustable vertically. For example, the seat legs 30 may telescope, or the seat portion 18 and attached back rest 22 may slide up and down along a component (for example, column) of an X-ray dental imaging system or otherwise be adjustable vertically up and down together to accommodate patients of different height.

With continued reference to FIGS. 1-6, the back rest 22 is pivotally coupled to the seat portion 18 (for example, to the support member 26 of the seat portion 18) with at least one hinge 34. The hinge 34 may include, for example, a pinned connection, a coiled spring or springs, a living hinge, or other type of structure that pivotally couples the back rest 22 to the seat portion 18. In the illustrated embodiment, the back rest 22 is a spring-loaded back rest 22 that is pivotally coupled to the seat portion 18 such that a top 38 (FIG. 1) of the back rest 22 is biased forward (for example, along a counter-clockwise direction as illustrated in FIG. 1) and toward a folded down position relative to the support member 26. The hinge 34 may include a spring or other biasing member (for example coil, gas, magnetic, or gravity spring) to bias the back rest 22 forward. Additionally or alternatively, a separate biasing member (for example, a spring, actuator, or other biasing member) presses against the back rest 22 from behind the back rest 22 to bias the back rest 22 in the forward direction. In some examples, rather than being pivotally coupled to the seat portion 18, the back rest 22 may slide (for example translate or shift linearly along a rail or other structure) relative to the seat portion or otherwise move relative to the seat portion 18. The adjustments modifying the relative positions of the seat portion 18, back rest 22, and a head rest 42 of the apparatus 10 described further herein accommodate large anatomical variations in the bodies and backs of patients. The head rest 42 may be tied to or otherwise correspond to an imaging area and it may be adjustable to a limited degree, to account for head size variations which may be relatively close from patient to patient as compared to larger anatomical variations in the bodies and backs of patients.

With continued reference to FIGS. 1-6, the head rest 42 may be fixed. For example, the head rest 42 may be fixed to a component of an X-ray dental imaging system, or to another component (for example, a wall or support post), such that the head rest 42 is fixed in space. The head rest 42 may be fixed to a component of an X-ray dental imaging system such that the head rest 42 is constrained relative to an imaging area (for example a field of view or volume of interest). The head rest 42 is separate from and spaced from the chair 14. In other embodiments, the head rest 42 may be adjustable in one or more degrees of freedom (for example vertically up and down) before or after a patient's head is in position for a scan. For example, the head rest 42 may include a screw-based adjustment that is driven by a motor or manually.

Figure 4:
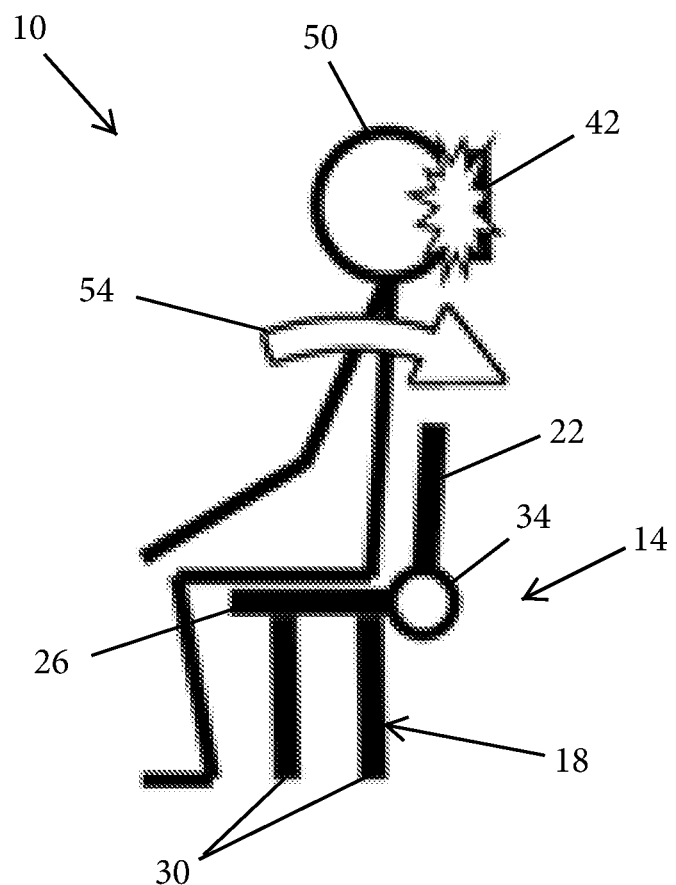
FIG. 4 is a schematic view of the patient's head hitting a head rest.
Figure 5:
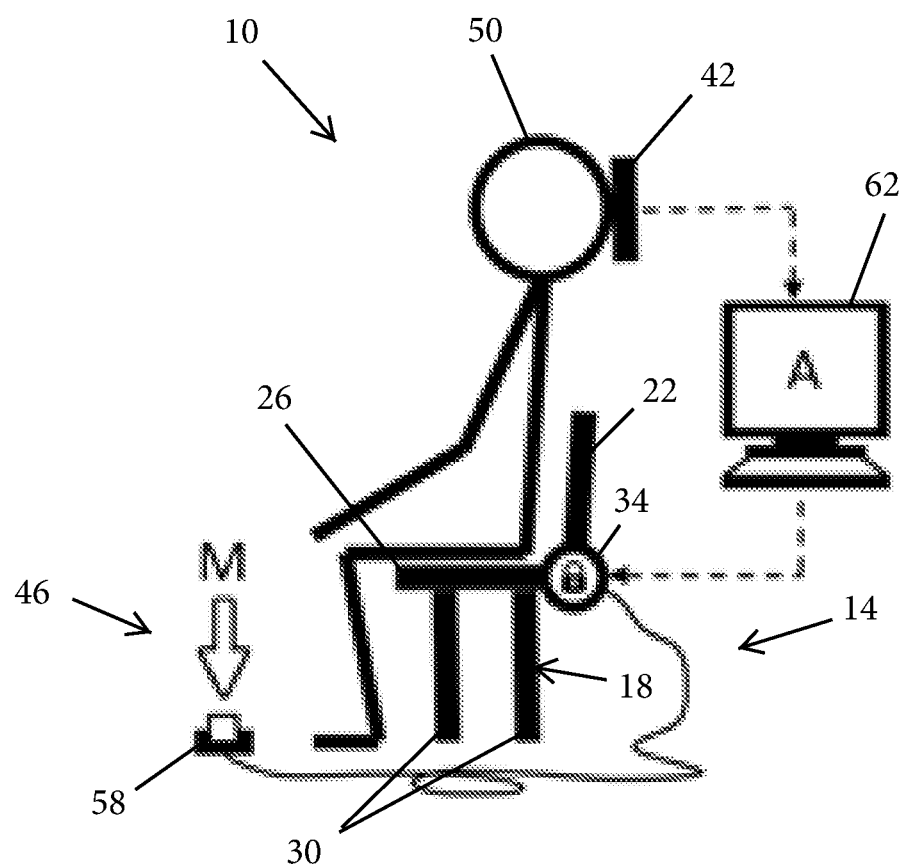
FIG. 5 is a schematic view of the back rest being locked manually and/or automatically.

With reference to FIG. 5, the chair 14 includes a locking system 46 to lock a position of the back rest 22 relative to the seat portion 18. The locking system 46 may allow a continuum of positions (for example by using a friction block or brake) or incremental locking steps (for example using ratchet or dowel locks). During use, a patient 50 sitting on the apparatus 10 may lean back against the back rest 22 and move (for example rotate) the back rest 22 (for example backwards along a clockwise direction 54 as seen in FIG. 4). In some examples, the back rest 22 may move or push forward to accommodate and follow a patient who is leaning forward (for example to correct a position). When the patient stands, the back rest 22 may also push forward and assist the patient in standing up. When the patient is sitting and the patient's head hits the head rest 42 (as depicted in FIG. 4), the patient 50 (or an operator, a medical technician, or dental technician) may then lock the position of the back rest 22. The locking system 46 may include a pin (for example a dowel) or other locking structure that is moved manually and engages (for example, is inserted through an aperture in) the back rest 22 to lock movement (for example linear or rotational movement) of the back rest 22 relative to the seat portion 18. The pin or other locking structure may also engage the seat portion 18, or another component, to lock relative movement of the back rest 22. With reference to FIG. 5, the locking system 46 may include a switch 58 (for example, a button) that is actuated or pressed manually by the patient's foot or an operator's foot. In one example, the switch 58 controls a linear actuator or electric motor, which causes the pin or other locking structure to be moved to engage the back rest 22 and to lock movement of the back rest 22. The switch 58 may be connected to the actuator or motor via a wired or wireless connection. In some examples, a lever may be manually pulled or otherwise activated to activate an electrical or mechanical actuator and to lock the back rest 22.

In one alternative, the locking system 46 is instead an automatic locking system. In the example illustrated in FIG. 5, a controller 62 detects (via information provided by a presence sensor) when the patient's head contacts the head rest 42, and then sends a signal to the locking system 46 to move the pin or other locking member to lock the position of the back rest 22. As noted, the pin or other locking structure may be moved for example by a linear actuator or other element. The head rest 42 may include a presence sensor (for example, a compression switch, pressure sensor, capacitive sensor, etc.) that detects the presence of the patient's head on the head rest 42, and sends a signal to the controller 62 when the patient's head hits the head rest 42. When the patient's head disengages the head rest 42 and/or the sensor no longer detects the presence of the patient's head on the head rest 42, the sensor sends another signal or new information to the controller 62, and the pin or other locking member is moved again to allow movement of the back rest 22. In some examples, the patient 50 may begin to lean back on the back rest 22 and the back rest 22 may move (for example rotate) along the direction 54. Once the patient 50 stops leaning back (or slows down), the back rest 22 may automatically lock in place (for example, via a spring-loaded pin, ratchet, or other mechanism). In some examples, the detection of the patient's head against the head rest 42 may be determined or verified by using pre-determined parameters that define details of the patient's anatomy for positioning, and/or by using sensors (for example cameras) that identify patient position.

The locking system 46 may also lock other movements of the chair 14. For example, the patient or operator may be able to manually lock a rotation of the overall chair 14 about a vertical axis, or lock a vertical movement of the chair 14 along the vertical axis. The locking system 46 may include additional pins or other locking structures that permit locking of the other movements of the chair 14. The locking system 46 may also automatically lock the other movements of the chair 14. For example, when the patient's head hits the head rest 42, the controller 62 may automatically lock not only the rotational position of the back rest 22, but also the rotation of the chair 14 overall as well as the vertical height of the chair 14.

As illustrated in FIGS. 1-6, the apparatus 10 allows patients 50 of various sizes and shapes to be seated, and for each patient's head to contact the head rest 42 in an identical or substantially identical location, regardless of the shape and size of the patient.

Figure 2:
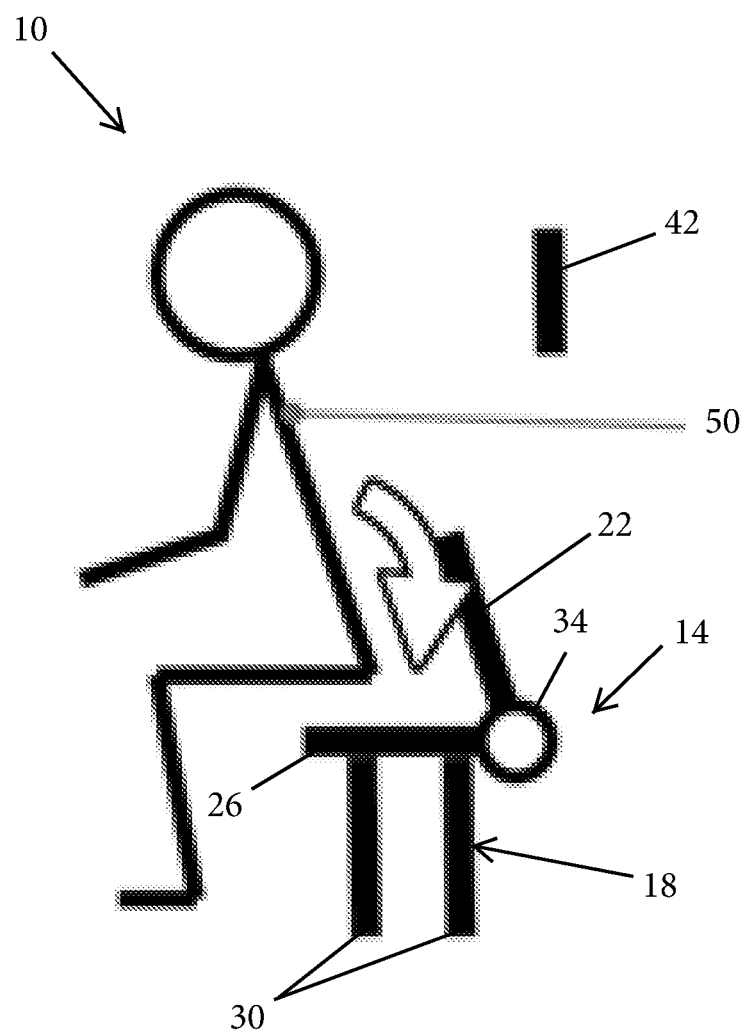
FIG. 2 is a schematic view of a patient seated on the apparatus.
Figure 3:
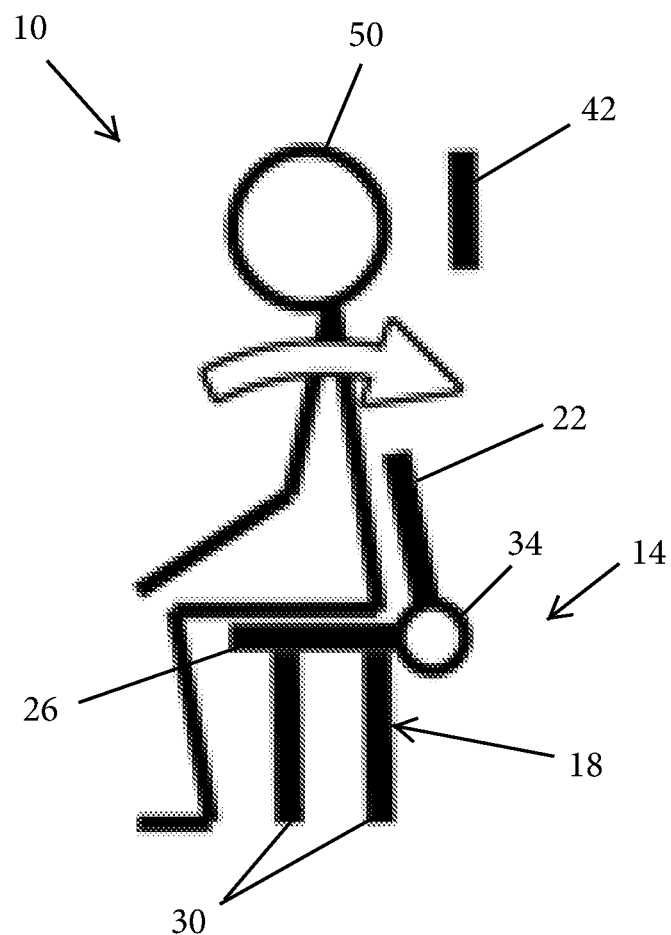
FIG. 3 is a schematic view of the patient leaning back against a back rest of the apparatus.

With reference to FIG. 1, during use the back rest 22 may initially be in a default position. The back rest 22 is biased forward and is leaning down toward the support member 26. With reference to FIGS. 2 and 3, the patient 50 then sits down on the support member 26 and begins to slide back and lean his or her back against the back rest 22. As noted above, patients 50 may be of any shapes or sizes, and may have backs of various sizes and curvatures. As the patient leans back, the back rest 22 follows the patient's back dynamically, and adjusts to the patient's position.

With reference to FIG. 4, the back rest 22 eventually moves backwards until the patient's head contacts the head rest 42 and/or the patient is in, or close to, a desired position. As described above, and as illustrated in FIG. 5, at this point the movement of the back rest 22 may be locked manually (M) or automatically (A).

Figure 6:
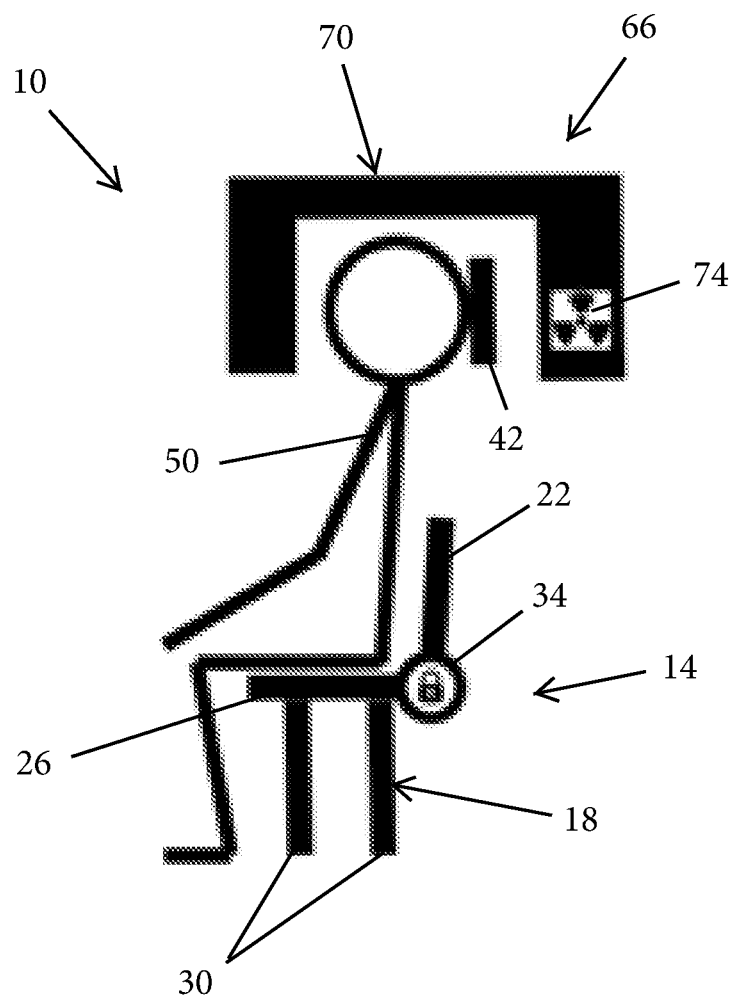
FIG. 6 is a schematic view of an X-ray dental imaging system being used in combination with the apparatus.

With reference to FIG. 6, once the back rest 22 is locked, the patient is then positioned for a medical procedure. For example, FIG. 6 illustrates a portion of an X-ray dental imaging system 66. The X-ray dental imaging system 66 includes a rotating part 70 (arm or gantry arm) that includes an X-ray source 74. As illustrated in FIG. 6, the rotating part 70 may rotate about the patient's head and the head rest 42 (the head rest 42 being fixed, for example, to another component of the X-ray dental imaging system 66) to obtain an X-ray image (for example, a computed tomography (CT) scan). The rotating part 70 may be C-shaped, and coupled to a movable upper shelf. The rotating part 70 may further include an X-ray detector. As illustrated in FIG. 6, the head rest 42 is in, or close to, a desired imaging volume. For example, the head rest 42 may be tied to or otherwise correspond to an imaging area. In some examples, the head rest 42 may be adjustable to a limited degree, to account for head size variations, which may be relatively close from patient to patient as compared to larger anatomical variations in the bodies and backs of patients.

Figure 7:
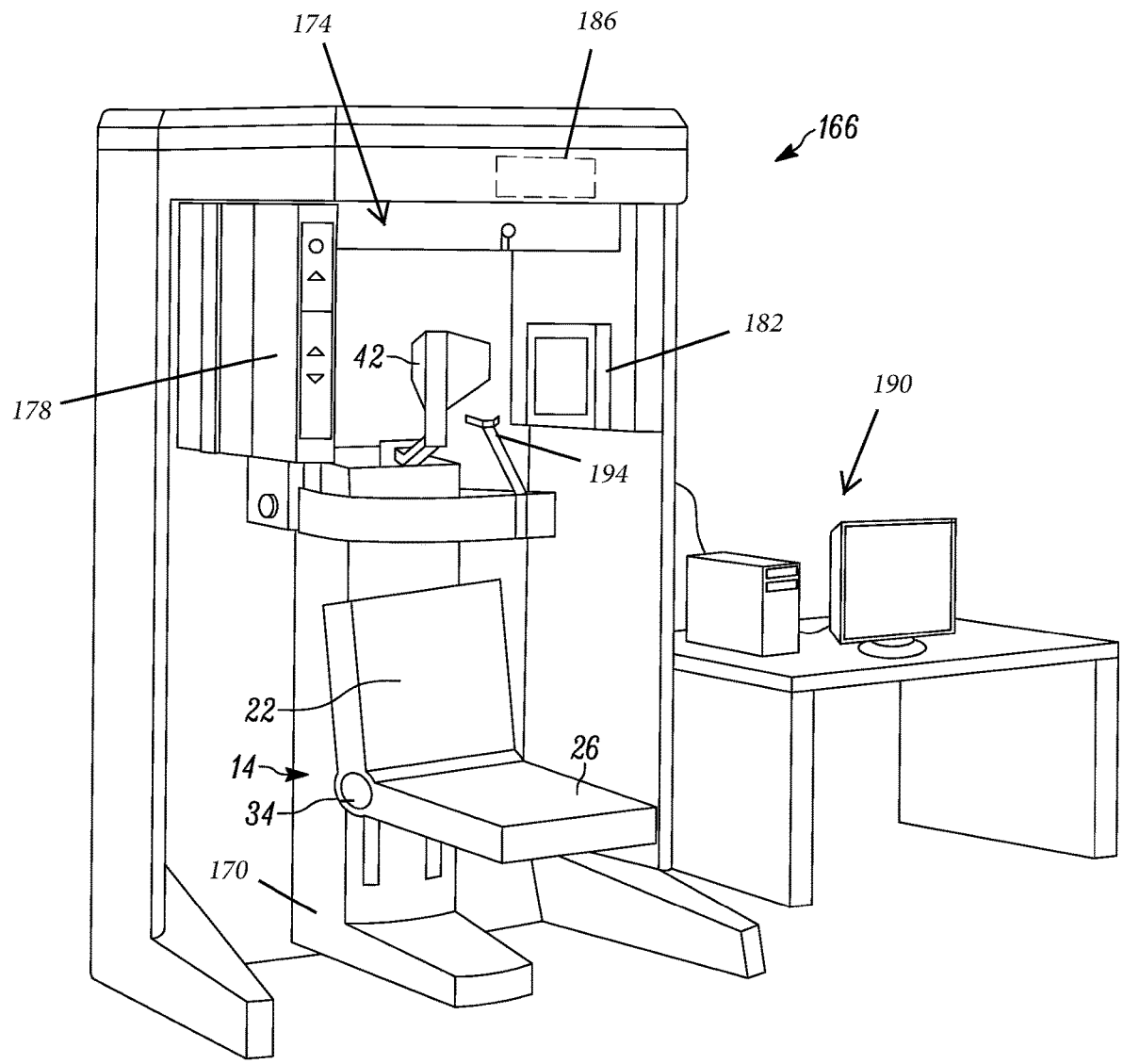
FIG. 7 is a perspective view of another kind of X-ray imaging system that may be used in combination with the apparatus.
Figure 8:
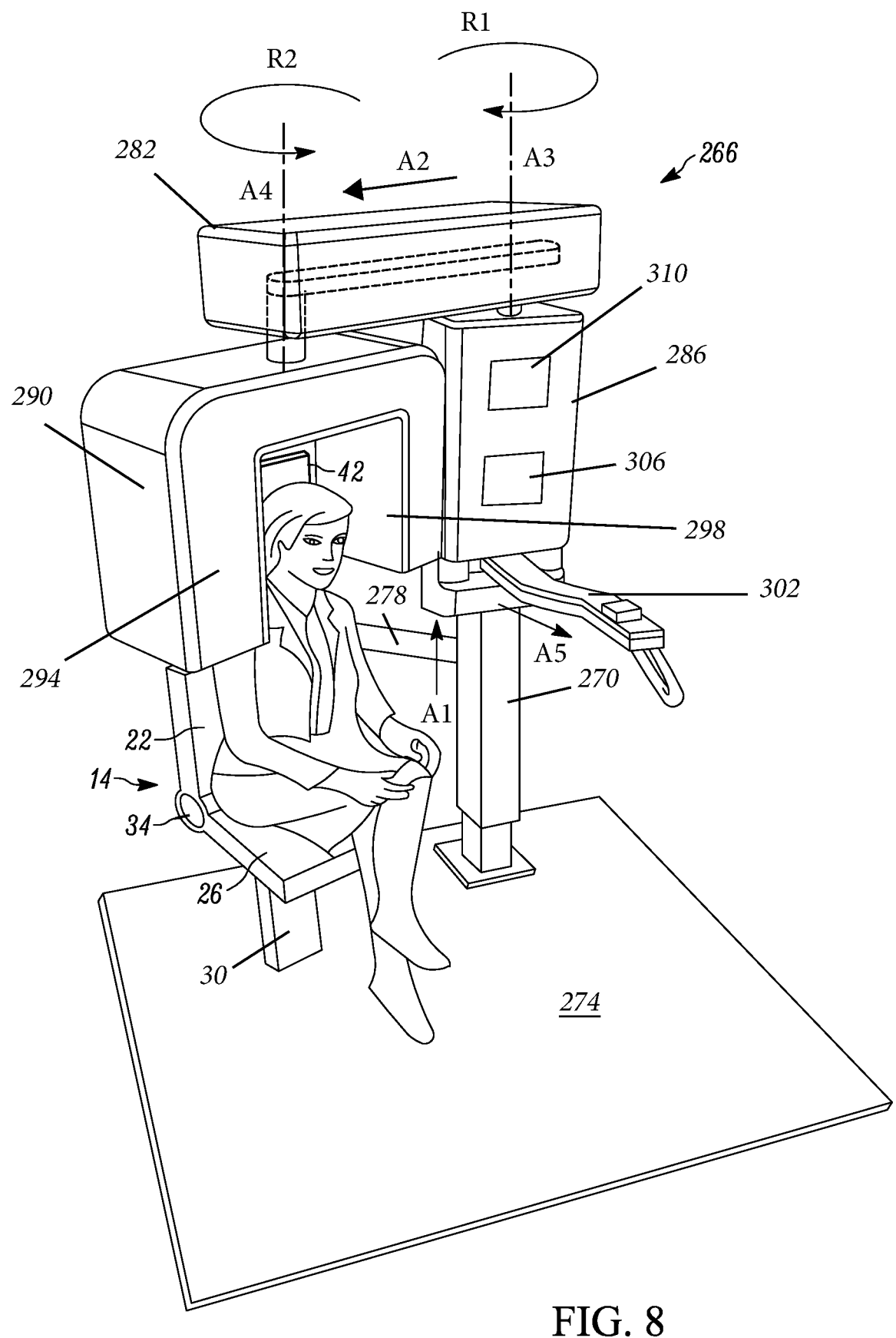
FIG. 8 is a perspective view of another kind of X-ray dental imaging system that may be used in combination with the apparatus.

The apparatus 10 may be used in various settings and with various systems, including but not limited to X-ray dental imaging systems. FIGS. 7 and 8, for example, illustrate examples of other X-ray dental imaging systems 166, 266 respectively that include a version of the patient positioning apparatus 10 incorporated into the system.

For example, in FIG. 7 the system 166 includes a column 170. The chair 14 slides vertically up and down along the column 170, and does not include legs. The system 166 also includes a rotating part 174 (for example, arm or gantry arm) with an X-ray source 178 and a detector unit 182. The system 166 may also include an on board computer or processor 186, and a computer 190. During a scan, a patient sits on the chair 14 and may place his or her chin on a chin support 194. The rotating part 174 is rotated around the patient's head, and, as the rotating part 174 rotates, the X-ray source 178 moves and directs radiation at the patient's head at various angles. In some examples the head rest 42 in this system 166 may be fixed permanently to the column 170, or may have some limited adjustability relative to the column 170 (for example to account for head size variations).

In FIG. 8, the system 266 includes a column 270. The column 270 extends for example vertically upward from and transverse to a frame 274 in a lengthwise direction, as denoted by arrow A1. The frame 274 may be positioned at a variety of locations within a room, for example on or fixed to a floor panel, integrated as part of a floor panel, positioned on or fixed to a wall (for example, without contacting a floor panel), or integrated as part of a wall. The chair 14 is spaced from the column 270 and includes a single leg 30 coupled for example to the frame 274. The head rest 42 is coupled to a post 278 that extends over to the column 270. The head rest 42 may be fixed permanently to the post 278 and/or to the column 270 in this system 260. In some examples, the head rest 42 may have some limited adjustability relative to the post 278 and/or the column 270 (for example to account for head size variations). The system 266 also includes an upper shelf 282 (for example, arm or top support member) that is coupled to the column 270 and/or to a housing 286 generally at an upper end of the housing 286. The upper shelf 282 is oriented along a lengthwise direction, as indicated by arrow A2, transverse to the lengthwise direction A1, and has a length along the lengthwise direction A2 beyond the housing 286 in at least one direction to create an overhang. A proximal end of the upper shelf 282 is rotatably coupled to the column 270 and/or to the housing 286 about a first axis A3 such that the upper shelf 282 is rotatable around the column 270 about the first axis A3 in a first rotational direction R1 (and/or a direction opposite to the first rotational direction R1). For example, the upper shelf 282 may rotate up to 400 degrees (or other values and ranges) about the first axis A3 between a first position about an object to a second position about the object. A motor may be located in the upper shelf 282 or in the column 270 to rotate the upper shelf 282. The upper shelf 282 may also be translated (for example via a motor) vertically relative to the column 270 (for example, sliding vertically along a track, via a screw shaft, etc.)

The system 266 further includes a rotating part 290 (for example, arm or gantry arm) rotatably coupled to the upper shelf 282. The rotating part 290 may be a C-shaped gantry arm sized to fit and rotate around an object, for example a patient's head. The rotating part 290 may instead be U-shaped, or have other shapes and sizes than that illustrated. The rotating part 290 is rotatably mounted to the upper shelf 282 about a second axis A4, spaced apart from and parallel to the first axis A3. The rotating part 290 rotates in a second rotational direction R2 (and/or a direction opposite to the second rotational direction R2). For example, the rotating part 290 may rotate up to 400 degrees (or other values and ranges) about the second axis A4. The rotating part 290 is capable of rotating entirely about an object, for example a patient's head. The rotating part 290 and/or the upper shelf 282 includes one or more actuators, for example a motor-driven track or rail system to provide linear movement (for example along the direction A2) of the rotating part 290 relative to the upper shelf 282.

The rotating part 290 supports an X-ray source 294 and a detector unit 298. The X-ray source 294 generates an X-ray beam, and the detector unit 298 detects the X-ray beam. The X-ray source 294 and the detector unit 298 are positioned opposite one another such that a head of a patient (for example, child or adult) can be positioned therebetween to produce (for example, provide data for), for example, a panoramic, computed tomography, or cephalometric image. In some examples a beam limiting device may be affixed to the X-ray source 294 to control a width and height of the X-ray beam emitted from the X-ray source 294.

The system 266 also includes a lower shelf 302 (for example, arm) that is coupled to the housing 286 or column 270. The lower shelf 302 may be rotatably coupled to the housing 286 or column 270. For example, as illustrated in FIG. 8, the lower shelf 302 may rotate (for example, pivot) horizontally relative to the housing 286 (for example generally about a vertical axis that is parallel to the direction A1).

The lower shelf 302 may be a frame member that extends generally in a lengthwise direction, as indicated by arrow A5 transverse to the lengthwise direction A1 of the column 270. The lower shelf 302 may be rotatable relative to the housing 286 or column 270, and translate along the length of the column 270 (for example, vertically up and down) with the housing 286. The lower shelf 302 may accommodate a patient at various heights and positions, for example for a standing patient and a seated patient such as that in FIG. 8.

The system 266 may also include a controller 306 (for example, a microprocessor, memory, and related components). The controller 306 is programmed to control various aspects of the system 266. For example, the controller 306 can be programmed to receive operator input via an input device, produce an output via the X-ray source 294, cause motors or similar devices to rotate the upper and/or lower shelves 282, 302 about the first rotational axis A3, and rotate the rotating part 290 about the second rotational axis A4. The controller 306 can signal a motor 310 to rotate the upper shelf 282 until the rotating part 290 is positioned around the head of the patient. If the patient is seated, the controller 306 can use inputs (for example, from sensors) to determine a distance between the chair 14 and the column 270 to approximate or determine the desired position of the rotating part 290. The controller 306 can also actuate the motor 310 to translate the rotating part 290 along the upper shelf 282, translate the upper shelf 282 and/or housing 286 along the column 270 and/or rotate the lower shelf 302 relative to the housing 286 or column 270.

The apparatus 10 may also be used with other imaging systems, or with any other medical systems where it is desired to obtain a consistent positioning of patient heads when the patients are sitting. Overall, the apparatus 10 makes patient positioning easier, and helps ensure that the patient's head is located at the same location. The apparatus 10 also provides an operator the opportunity to take higher-quality X-ray images regardless of patient size and shape. Thus, by using the apparatus 10, it may be easier and faster to position differently-sized and shaped patients to a desired position.

Various features, aspects, and embodiments are set forth in the following claims.

What is claimed is:

1. A patient positioning apparatus for an X-ray dental imaging system, the patient positioning apparatus comprising:
    a head rest; and
    a chair separate from and spaced from the head rest, the chair having a seat portion and a back rest coupled to the seat portion, wherein the chair further includes a locking system configured to lock a position of the back rest relative to the seat portion,
    wherein the locking system includes a controller, and a sensor coupled to the head rest, and wherein the sensor is configured to detect a patient's head contacting the head rest and send a signal to the controller to lock the position of the back rest relative to the seat portion.

2. The apparatus of claim 1, wherein the head rest is fixed in space.

3. The apparatus of claim 2, wherein the head rest is fixed to a portion of an x-ray dental imaging system.

4. The apparatus of claim 1, wherein the locking system includes a locking pin configured to engage the back rest to lock the position of the back rest relative to the seat portion.

5. The apparatus of claim 1, wherein the chair is vertically adjustable.

6. The apparatus of claim 1, wherein the chair includes a support member and a seat leg extending below the support member, wherein the back rest is pivotally coupled to the support member.

7. The apparatus of claim 1, wherein the chair includes a biasing member configured to bias the back rest in a first direction.

8. The apparatus of claim 7, wherein the first direction is toward the seat portion.

9. The apparatus of claim 7, wherein the chair includes a hinge, and wherein the biasing member is a coiled spring in the hinge.

10. The apparatus of claim 7, wherein a patient is configured to sit on the chair and to lean back against the back rest to move the back rest in a second, opposite direction.

11. An X-ray dental imaging system comprising:
    the apparatus of claim 1.

12. The X-ray dental imaging system of claim 11, further comprising a rotating part having an X-ray source and detector.

13. The X-ray dental imaging system of claim 12, wherein the rotating part is configured to rotate about the head rest and a patient's head in contact with the head rest.

14. The X-ray dental imaging system of claim 11, further comprising a column, wherein the head rest is fixed relative to the column.

15. The apparatus of claim 1, wherein the locking system is configured to lock an additional movement of the chair.

16. The apparatus of claim 15, wherein the additional movement includes at least one of a vertical or rotational movement of the chair.

* * * * *